United States Patent
Boehm et al.

(10) Patent No.: US 8,671,933 B2
(45) Date of Patent: Mar. 18, 2014

(54) INHALATION THERAPY DEVICE WITH MULTIPLE NOZZLES

(75) Inventors: Andreas Boehm, Reichling (DE); Martin Luber, Munich (DE); Sven Rosenbeiger, Starnberg (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 1313 days.

(21) Appl. No.: 12/226,120

(22) PCT Filed: Mar. 8, 2007

(86) PCT No.: PCT/EP2007/002030
§ 371 (c)(1),
(2), (4) Date: May 12, 2009

(87) PCT Pub. No.: WO2007/118557
PCT Pub. Date: Oct. 25, 2007

(65) Prior Publication Data
US 2009/0301473 A1   Dec. 10, 2009

(30) Foreign Application Priority Data
Apr. 11, 2006 (DE) .................... 10 2006 017 002

(51) Int. Cl.
*A61M 11/00* (2006.01)
*B05B 1/26* (2006.01)

(52) U.S. Cl.
USPC .............................. 128/200.21; 128/200.18

(58) Field of Classification Search
USPC ............ 128/200.11, 200.13, 200.14, 200.18, 128/200.21, 203.12, 203.16
See application file for complete search history.

(56) References Cited

U.S. PATENT DOCUMENTS

| | | | | |
|---|---|---|---|---|
| 3,097,645 A | * | 7/1963 | Lester | 128/200.21 |
| 3,584,792 A | * | 6/1971 | Johnson | 239/424 |
| 4,757,812 A | | 7/1988 | Arborelius, Jr. | |
| 5,533,501 A | * | 7/1996 | Denyer | 128/200.21 |
| 5,738,086 A | * | 4/1998 | McMahon et al. | 128/200.21 |
| 5,823,179 A | * | 10/1998 | Grychowski et al. | 128/200.18 |

(Continued)

FOREIGN PATENT DOCUMENTS

| | | |
|---|---|---|
| DE | 1 147 355 | 4/1963 |
| DE | 3429411 | * 2/1986 |

(Continued)

OTHER PUBLICATIONS machine translation of JP2005-230799.*

(Continued)

*Primary Examiner* — Kristen Matter
(74) *Attorney, Agent, or Firm* — Wolf, Greenfield & Sacks, P.C.

(57) ABSTRACT

To increase the efficacy of atomizer nozzles operating with compressed gas, an atomizer device for inhalation therapy appliances includes means for delivering a compressed gas, in particular compressed air; means for supplying a fluid that is to be atomized, in particular a therapeutic liquid; several compressed gas outlet openings from which a delivered compressed gas emerges; and several fluid outlet openings from which the fluid to be atomized emerges on account of the emerging compressed gas. The atomizer device includes at least three compressed gas outlet openings arranged in a row, and one of the compressed gas outlet openings is in each case assigned at least two fluid outlet openings which, together with the associated compressed gas outlet opening, form an atomizer nozzle.

14 Claims, 3 Drawing Sheets

(56) References Cited

U.S. PATENT DOCUMENTS

| | | | |
|---|---|---|---|
| 6,044,841 A * | 4/2000 | Verdun et al. | 128/200.18 |
| 6,318,640 B1 * | 11/2001 | Coffee | 239/3 |
| 6,405,944 B1 * | 6/2002 | Benalikhoudja | 239/338 |
| 6,796,513 B2 * | 9/2004 | Fraccaroli | 239/338 |
| 8,196,573 B2 * | 6/2012 | Fink et al. | 128/200.14 |
| 2004/0177849 A1 * | 9/2004 | Del Bon | 128/203.12 |
| 2005/0120947 A1 | 6/2005 | Sone et al. | |
| 2006/0162722 A1 * | 7/2006 | Boehm et al. | 128/200.14 |

FOREIGN PATENT DOCUMENTS

| | | |
|---|---|---|
| EP | 0 170 715 A1 | 2/1986 |
| EP | 0 261 649 A2 | 3/1988 |
| EP | 1 417 982 A2 | 5/2004 |
| FR | 401 698 | 9/1909 |
| JP | 61-500714 | 4/1986 |
| JP | 02-116379 | 5/1990 |
| JP | 09-248502 | 9/1997 |
| JP | 2000-504603 | 11/2004 |
| JP | 2005-230799 | 9/2005 |
| WO | WO 97/29799 | 8/1997 |

OTHER PUBLICATIONS

International Preliminary Report on Patentability issued Oct. 14, 2008 for corresponding International Application No. PCT/EP2007/002030.

* cited by examiner

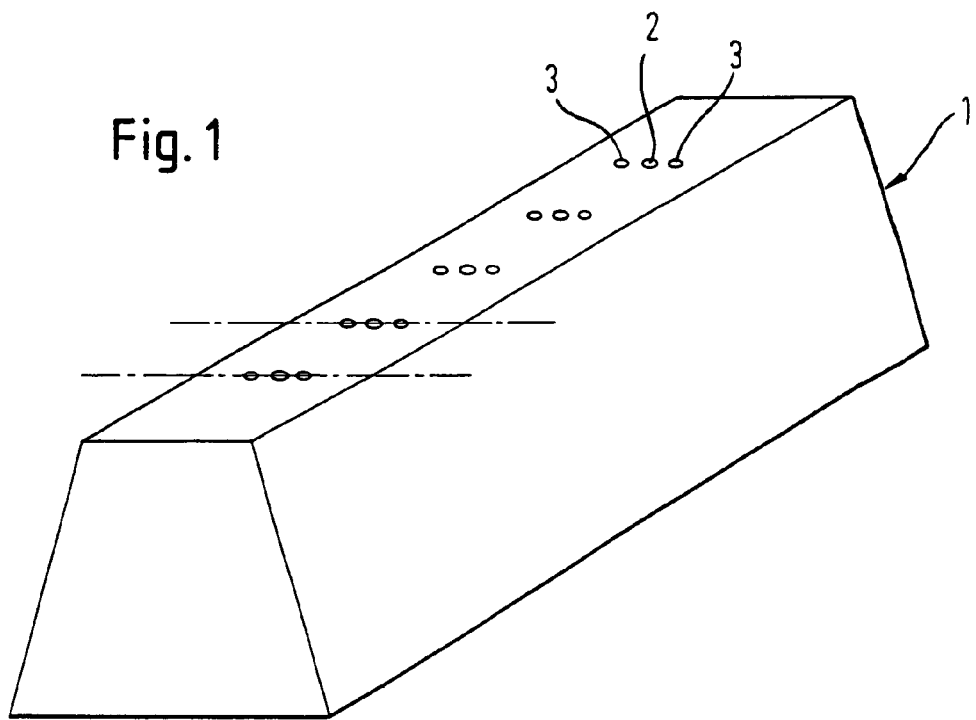
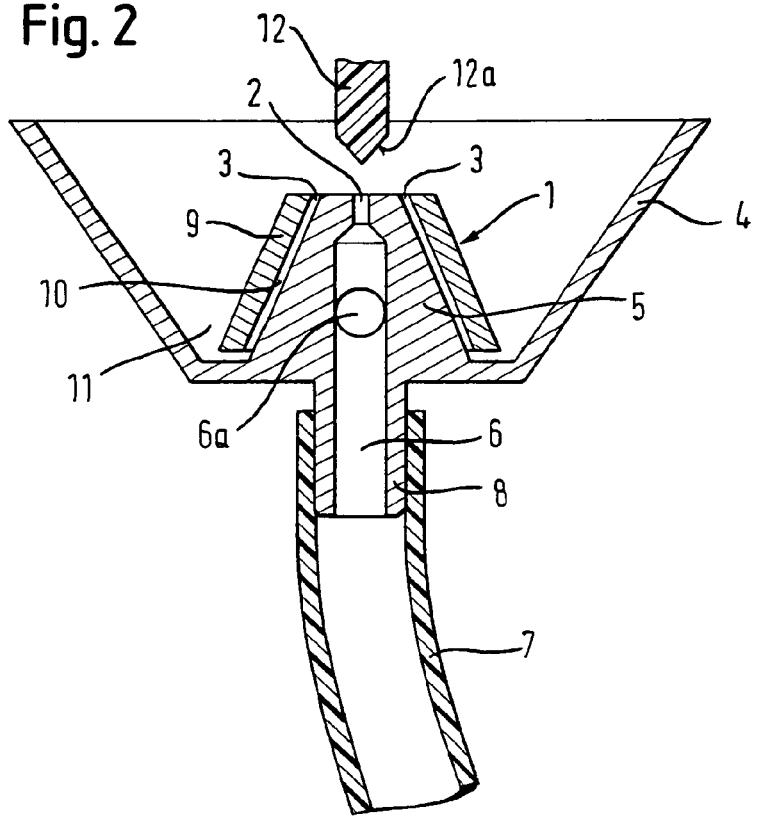

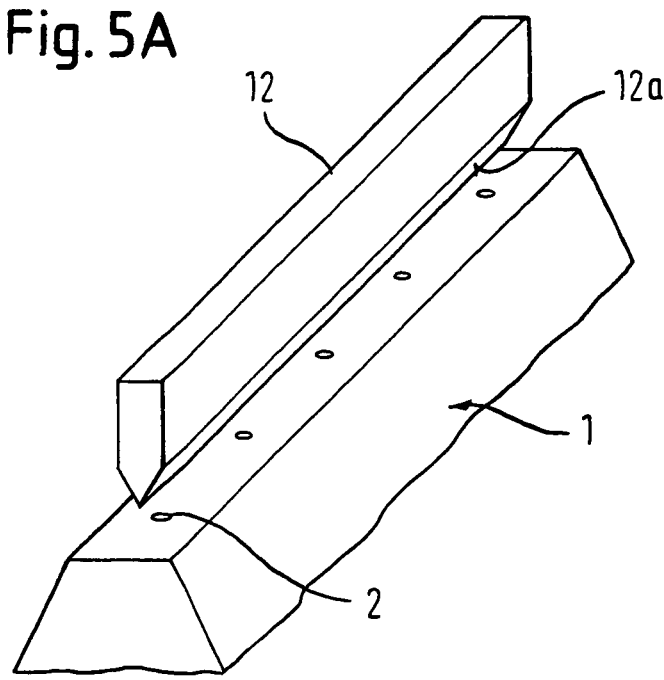
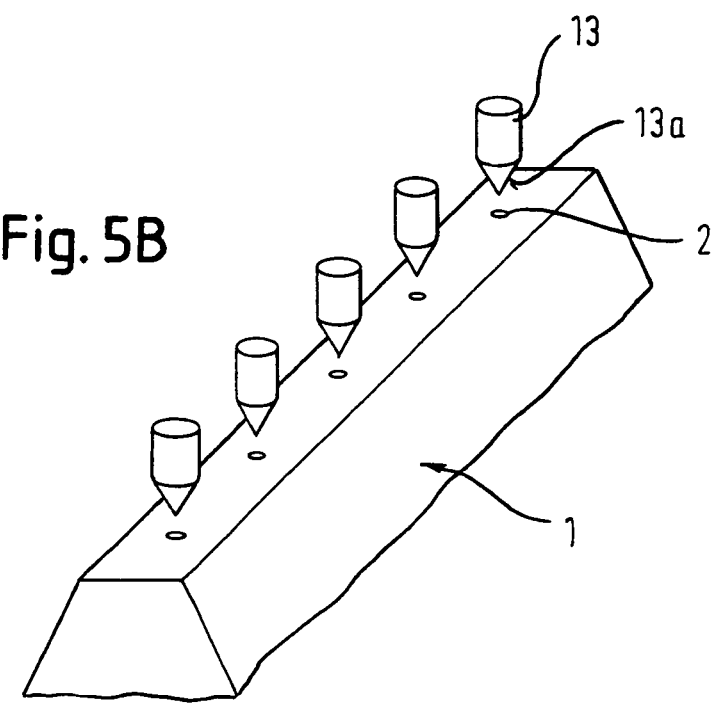

INHALATION THERAPY DEVICE WITH MULTIPLE NOZZLES

FIELD OF THE INVENTION

The invention relates to a nebuliser device for inhalation therapy apparatus for nebulising a fluid, in particular a therapeutically effective liquid.

DISCUSSION OF THE RELATED ART

Nebuliser nozzles for inhalation therapy apparatus for nebulising liquid or powder substances have been known for a long time in the prior art, in which nebulisation takes place with the help of compressed air or another pressure medium supplied to the nebuliser nozzle. DE-AS 1 147 355 already describes such a nebuliser nozzle, with the disclosed nebuliser nozzle displaying the basic structure and having a channel for the pressure medium arranged centrally in the nozzle and suction channels that are arranged adjacent thereto. When the supplied compressed air emerges from the outlet opening of the pressure medium channel, the liquid to be nebulised is sucked through the suction channels and nebulised in the compressed air outlet area. Nebuliser nozzles having this basic structure were further developed and improved over time and additional elements were added. To improve the nebuliser nozzle, DE-AS 1 147 355 already describes a gas flow control opposite the outlet opening for the pressure medium, which has a cuneiform surface in the direction of the outlet openings. Measures which increase the efficiency of the nebuliser nozzle or the inhalation therapy apparatus comprising the nebuliser nozzle are also known from other publications, such as, for example, EP 0 170 715 A or EP 0 261 649 A.

Considerable experience is accordingly available as regards the construction of these nozzles. Furthermore, suitable compressed gas sources, for example portable compressors, have been developed, which have been continually optimised over time.

SUMMARY

The invention aims at further improving and in particular increasing the efficiency of nozzle nebulisers.

This aim is achieved by a nebuliser device having the features of claim 1, Advantageous designs can be found in the sub-claims.

BRIEF DESCRIPTION OF THE DRAWINGS

The invention will be explained in more detail in the following by means of embodiments and with reference to the drawings.

FIG. 1 shows a schematic and simplified view of an embodiment of a nebuliser device according to the invention;

FIG. 2 shows a sectional view of the embodiment of a nebuliser device according to the invention in connection with a fluid container;

FIG. 5A show the design of a gas flow control or baffle and 5B rods.

DETAILED DESCRIPTION

Figure 3A:
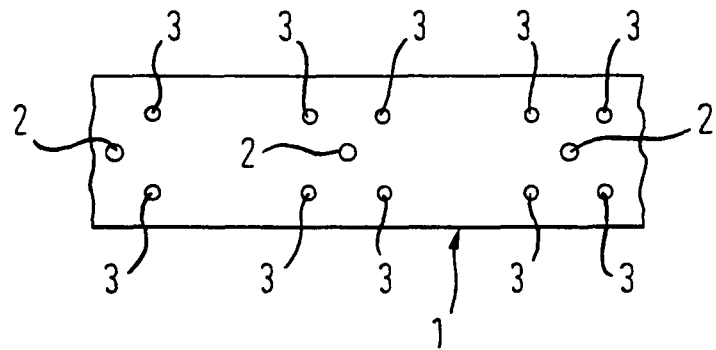
FIG. 3A show a simplified view of different designs of the and 3B fluid outlet openings.

FIG. 1 shows a schematic and simplified view of a nebuliser device 1 according to the invention, in which in particular the arrangement of the compressed gas outlet openings 2 and the associated fluid outlet openings 3 is shown. Further details that are not shown in FIG. 1 are apparent from the description of the remaining figures as provided further below.

As is apparent in FIG. 1, a plurality, however at least three openings 2 are provided in a nebuliser device 1 according to the invention, out of which a compressed gas supplied to the device can emerge and which are arranged in a row. The nebuliser device 1 according to the invention therefore has an elongated basic shape, as is apparent from FIG. 1. Allocated to each compressed gas outlet opening 2 are at least two openings 3, out of which a fluid to be nebulised can emerge. In the example shown in FIG. 1, the fluid outlet openings 3 are arranged in a row with the compressed gas outlet opening 2. In other words, in the example shown in FIG. 1, the compressed gas outlet opening 2 and the two fluid outlet openings 3 are arranged in a straight line. This row is preferably arranged perpendicular to the row of compressed gas outlet openings 2, as is also shown in FIG. 1.

When the supplied compressed gas emerges from the compressed gas outlet openings 2, a fluid supplied to the fluid outlet openings is nebulised to form an aerosol in the region in front of the outlet openings 2, 3. Each compressed gas outlet opening 2, together with the fluid outlet openings 3 allocated thereto, forms a quasi independent nebuliser nozzle, with the efficiency of the nebuliser device 1 according to the invention, with its plurality of nebuliser nozzles 2, 3, surprisingly being better on the whole than the efficiency of a single nebuliser nozzle that is designed such that the area of the single compressed gas outlet opening corresponds to the total area of the plurality of compressed gas outlet openings 2 according to the invention. This aspect shall be clarified in the following by means of a calculation example.

In a typical nebuliser nozzle of the previously known type, the diameter of the compressed gas outlet opening is, for example, 0.48 mm, which results in an outlet area for the compressed gas of 0.181 mm². The compressed gas outlet opening furthermore has a circumference of 1.51 mm. In a nebuliser device according to the invention, the individual compressed gas outlet openings have a diameter, for example, of 0.2 mm, and thus the outlet area is 0.031 mm² and the circumference of the outlet openings is 0.63 mm. In order to provide approximately the same nozzle area, about five (or six) individual nozzles with a diameter of 0.2 mm are to be arranged in a row in a nebuliser device according to the invention, in accordance with the ratio of the area of the individual nozzles to the outlet area of a conventional nozzle; in the example illustrated above, this ratio is 5.84:1 (=0.181/0.031). Several advantages are achieved by retaining the area for the exit of the compressed gas. It is, for example, possible to make use of experience with conventional one-nozzle nebulisers, and thus already available empirically established values can be used for construction. Furthermore, a nebuliser device according to the invention can be used with the conventionally employed compressed gas sources, in particular the available compressors. It is not necessary to adapt the compressors since approximately the same compressed gas outlet area is also available in the nebuliser device according to the invention for the exit of the compressed gas.

In spite of the approximately equalised area of the compressed gas outlet openings 2 of a nebuliser device 1 according to the invention, the design of the nozzle arrangement according to the invention leads to an increase in the efficiency of nebulisation. According to the invention, this is achieved at an unchanged effective nozzle area owing to the enlargement of the fluid/compressed gas interface, which is substantially determined by the circumference of the outlet openings 2, between the nozzle spray and the liquid to be nebulised as a result of an increased number of nozzles with a smaller diameter. If the effective nozzle areas remain the same and the interface is clearly higher, the energy expenditure as compared to a system with a single nozzle is constant, however efficiency is increased owing to the increased interface, i.e. more liquid is nebulised.

As already mentioned above, the equalisation of the total area of the compressed gas outlet openings 2 allows available compressor systems to also be used with a nebuliser device 1 according to the invention without modification, in comparison with conventional nozzles. However, owing to the increased efficiency, there is also the possibility of realising a nebuliser device with a smaller total nozzle area, which can be operated with an accordingly smaller compressor, nevertheless achieving therewith the same efficiency as a conventional system. The smaller compressor can then also be reduced in size so that the transportability of the therapy system, which substantially consists of the compressor and the nebuliser, is increased further.

FIG. 2 shows a nebuliser device 1 according to the invention in a fluid container 4 for the storage of a fluid to be nebulised. It is apparent in the sectional view of FIG. 2 that the nebuliser device 1 according to the invention that is shown herein has an inner body 5, in which the compressed gas channels 6 are formed. The compressed gas channels 6 are used to distribute the compressed gas that is supplied via a compressed gas hose 7 that is attached to a connecting piece 8 of the device. The compressed gas channels 6 in the inner body 5 of the nebuliser device 1 according to the invention open out into the compressed gas outlet openings 2, of which only one is shown in FIG. 2 owing to the sectional view. The inner body 5 of the nebuliser device 1 according to the invention as seen in FIG. 2 is formed integrally with the fluid container 4 and the connecting piece 8 in the shown embodiment.

An outer body 9, for example a sleeve or hood, is placed on the inner body 5 of the nebuliser device 1 according to the invention, with it being apparent in FIG. 2 that the outer body 9 and the inner body 5 contact one another at conically designed surfaces such that the outer body 9 is supported on the inner body 5. Fluid channels 10 are shown in the sectional view of FIG. 2, which lie in the section plane. A fluid stored in the container is supplied to the fluid outlet openings 3 through the fluid channels 10, for which purpose the fluid channels 10 each extend from the fluid outlet opening 3 into the storage area 11 of the container 4. Owing to this design, the nebuliser device 1 according to the invention works according to the Venturi principle since the compressed gas emerging from the compressed gas outlet opening sucks the liquid stored in the container through the fluid channels such that the liquid exits at the fluid outlet openings and is nebulised by the emerging compressed gas.

In addition to the compressed gas channel 6 that forms an extension of the connecting piece, a compressed gas channel 6a that extends transverse thereto in the longitudinal direction of the nebuliser device 1 according to the invention is also apparent in FIG. 2, which corresponds to the arrangement of the nozzle openings 2 according to the invention. This compressed gas channel 6a, together with other compressed gas channels which lead to the compressed gas outlet openings 2 and which correspond to the compressed gas channel section shown in FIG. 2, bring about the supply of compressed gas to the multiple nebuliser nozzles in accordance with the invention.

FIG. 3A shows, in a simplified top view, a nebuliser device according to the invention, in which four fluid outlet openings 3 are allocated to each compressed gas outlet opening 2. In this embodiment of the invention, the arrangement is diagonally crosswise in relation to the direction of the row of compressed gas outlet openings 2. The compressed gas outlet openings 2, together with the four associated fluid outlet openings 3, respectively form an independent nozzle in this arrangement as well. The number of fluid outlet openings 3 may also be higher.

Figure 3B:
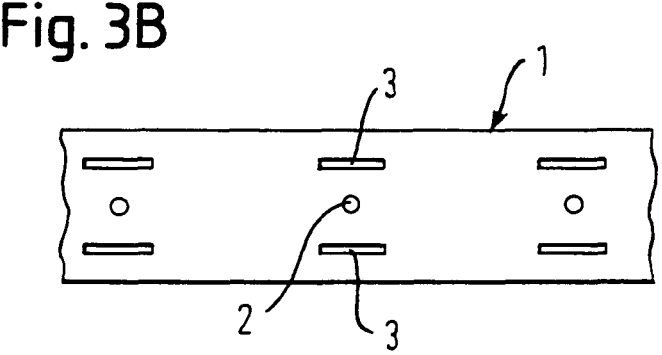

FIG. 3B shows, in a simplified top view, a design of the nebuliser device 1 according to the invention, in which the fluid outlet openings 3 are realised in the form of elongated slots. One slot is arranged on each of the two sides of the compressed gas outlet openings 2, with the longitudinal axis of the slots extending in the shown embodiment parallel to the straight line along which the compressed gas outlet openings 2 are arranged. The length of the slots can be freely selected to a large extent, however, in the case of longer slots, the width of the slots must be reduced so that the individual nozzles according to the invention nebulise the fluid effectively and work, for example, according to the Venturi principle.

Figure 4:
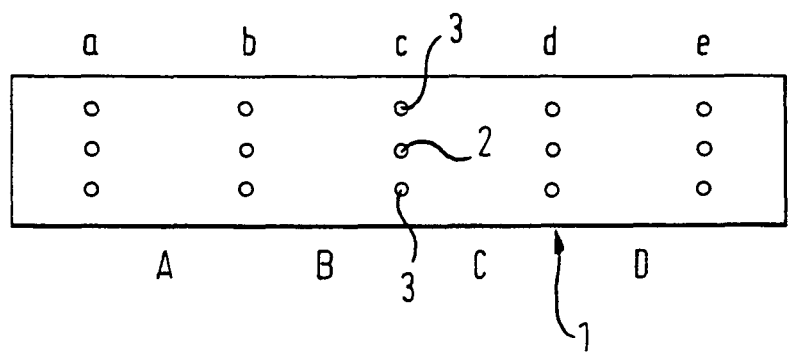
FIG. 4 shows a representation of the nozzle positions in order to explain the dimensions and arrangement.

FIG. 4 shows a simplified schematic view of the nozzle openings and serves to explain the selection of the measurements of the compressed gas outlet openings 2. The following table provides values for the diameter of the compressed gas outlet openings at each of positions a to e. The values for the distances A to D are in the magnitude of a few to several millimetres. The precise value is to be determined in each individual case inter alia depending on the number of fluid outlet openings and their diameter.

TABLE 1

| Example | a | b | c | d | e |
|---------|---|---|---|---|---|
| No. 1 | 0.2 mm | 0.2 mm | 0.2 mm | 0.2 mm | 0.2 mm |
| No. 2 | 0.15 mm | 0.2 mm | 0.2 mm | 0.2 mm | 0.15 mm |
| No. 3 | 0.1 mm | 0.15 mm | 0.25 mm | 0.15 mm | 0.1 mm |
| No. 4 | 0.1 mm | 0.1 mm | 0.3 mm | 0.1 mm | 0.1 mm |

It is apparent from table 1 that according to an advantageous embodiment of the invention, the size of the nozzle diameter increases towards the centre of the row of compressed gas outlet openings 2 if the nozzles do not have the same diameter.

TABLE 2

| Example | a | b | c | d | e |
|---------|---|---|---|---|---|
| No. 5 | 0.2 mm | 0.15 mm | 0.15 mm | 0.15 mm | 0.2 mm |
| No. 6 | 0.4 mm | 0.2 mm | 0.1 mm | 0.2 mm | 0.4 mm |
| No. 7 | 0.2 mm | 0.1 mm | 0.25 mm | 0.1 mm | 0.2 mm |
| No. 8 | 0.25 mm | 0.1 mm | 0.4 mm | 0.1 mm | 0.25 mm |

It is apparent from table 2 that according to further advantageous embodiments of the invention, the size of the nozzle diameter of the row of compressed gas outlet openings 2 can, to a large extent, be designed freely in respect of the desired nebulisation of the fluid or the geometry of the inhalation therapy apparatus in which the nebuliser device according to the invention is used.

The values in the tables are given purely as examples. The values must be determined in each individual case, for example by means of experiments, with it also being possible to take into consideration the properties of the fluid to be nebulised.

As shown in FIG. 2, the nebuliser device according to the invention has a gas flow control 12, which is arranged opposite the nozzle openings 2. In view of the basic shape of the nebuliser device that is elongated owing to the arrangement of the nozzle openings in a line, the gas flow control 12 is also configured in an elongated manner, as is shown in FIG. 5A. On the side facing the nozzle openings, the gas flow control 12 advantageously has a flat surface, a cuneiform surface 12a (see FIG. 5A), a rounded surface or a surface designed in another suitable manner. However, a baffle rod 13 respectively allocated to each individual nozzle of the nebuliser device 1 according to the invention (see FIG. 5B) can also be provided, which is arranged opposite the compressed gas outlet opening 2. On the side facing the opening, the baffle rod preferably has a pointed surface 13a (see FIG. 5B) or a rounded surface.

The invention claimed is:

1. Nebuliser device for inhalation therapy apparatus, comprising:
    an element for supplying a compressed gas, in particular compressed air;
    an element for supplying a fluid to be nebulised, in particular a therapeutically effective liquid;
    a plurality of compressed gas outlet openings, out of which the supplied compressed gas emerges; and
    a plurality of fluid outlet openings, out of which the fluid to be nebulised emerges owing to the emerging compressed gas:
    wherein
    at least three compressed gas outlet openings are arranged in a row; and
    at least two fluid outlet openings are allocated to each of the compressed gas outlet openings, which, together with the associated compressed gas outlet opening, form a nebuliser nozzle, and
    wherein
    the compressed gas outlet openings have diameters of less than 0.4 mm and at least two of the compressed gas outlet openings have diameters that are different from each other.

2. The nebuliser device according to claim 1, wherein the compressed gas outlet openings having larger diameters are arranged towards a centre of the row of compressed gas outlet openings.

3. The nebuliser device according to claim 1, wherein the compressed gas outlet openings having larger diameters are arranged at an edge of the row of compressed gas outlet openings.

4. The nebuliser device according to claim 1, wherein the diameters of the compressed gas outlet openings of the row of compressed gas outlet openings are symmetrically arranged to a centre of the row.

5. The nebuliser device according to claim 1, wherein a gas flow control is provided opposite the compressed gas outlet openings, said gas flow control being configured in an elongated manner to face the nebulizer nozzle openings being arranged in said row.

6. The nebuliser device according to claim 5, wherein the gas flow control has a surface facing the compressed gas outlet openings that is cuneiform or rounded.

7. The nebuliser device according to claim 1, wherein a baffle rod is provided for each compressed gas outlet opening, which is arranged opposite the compressed gas outlet opening.

8. The nebuliser device according to claim 7, wherein the baffle rod has a surface facing the compressed gas outlet openings that is pointed or rounded.

9. The nebuliser device according to claim 1, wherein the fluid outlet openings are circular.

10. The nebuliser device according to claim 1, wherein the fluid outlet openings are slots.

11. The nebuliser device according to claim 10, wherein the slots extend parallel to the row of compressed gas outlet openings.

12. The nebuliser device according to claim 1, wherein fluid channels extending to the fluid outlet openings are provided.

13. The nebuliser device according to claim 1, wherein the compressed gas outlet openings have a diameter of between 0.1 and 0.4 mm.

14. The nebuliser device according to claim 1, wherein the compressed gas outlet openings have a diameter of between 0.1 and 0.3 mm.

* * * * *